United States Patent [19]
Levin

[11] Patent Number: 6,006,120
[45] Date of Patent: Dec. 21, 1999

[54] CORDLESS PULSE OXIMETER

[75] Inventor: Paul D. Levin, Santa Cruz, Calif.

[73] Assignee: Palco Labs, Inc., Santa Cruz, Calif.

[21] Appl. No.: 09/177,091

[22] Filed: Oct. 22, 1998

[51] Int. Cl.[6] .................................................. A61B 5/00
[52] U.S. Cl. ............................................................. 600/323
[58] Field of Search ................................... 600/310, 316, 600/322, 323, 340, 344

[56] References Cited

U.S. PATENT DOCUMENTS 4,913,150  4/1990  Cheung et al. ......................... 600/323
5,490,523  2/1996  Isaacson et al. ....................... 600/323

*Primary Examiner*—Eric F. Winakur
*Attorney, Agent, or Firm*—Bruce H. Johnsonbaugh

[57] ABSTRACT

A replaceable sensing module is provided for use in a pulse oximetry device, allowing for quick replacement of a failed sensor element. A fingertip pad and a fingertip cover form the sensing module and cooperate to form a receptacle into which a patient's fingertip can be inserted. The sensing module has an internal spring, thereby permitting the module to be inserted into various oximetry type devices. The module has mounting rails and a multi-pin electrical connector, allowing a user to quickly replace the module in the event of component failure.

4 Claims, 9 Drawing Sheets

CORDLESS PULSE OXIMETER

BACKGROUND AND SUMMARY OF THE INVENTION

The invention relates to a cordless finger sensor for measuring blood oxygen saturation. More particularly, the present invention provides a module that fits into a special recess within an oximeter so that when in use, it becomes an integral part of the instrument. The invention allows for removal and replacement of the sensing module in case of component failure. Elimination of the sensor cable makes for easier carrying and storage of the device.

A small cordless oximeter in which all of the electronics are contained within the finger-gripping means is described in U.S. Pat. No. 5,490,523 to Isaacson et al. This device eliminates the external cord of a conventional oximeter and securely holds the patient's finger without support from the operator. Its external spring and lack of an internal pivot point prevent it from being used inside other devices. The design of the Isaacson oximeter also prevents the average user from replacing the sensor components in case of failure. In the event of LED or photodetector malfunction, the entire device is usually replaced.

A pulse oximeter with both replaceable and reusable components is taught by Swedlow et al in U.S. Pat. No. 5,209,250. Their device uses a conventional cord to connect the sensor to an oximeter. The replaceable part, containing only the LEDs, is wrapped over the end of the finger. The sensor has laterally extending adhesive webs which are then folded around the finger to hold the sensor in place.

Tobler et al in U.S. Pat. No. 5,645,440 describe a novel connector for oximeter sensors. This invention, assigned to Masimo, allows the user to quickly discard a disposable sensor at the end of a conventional cable and replace it with another one.

The sensor to be described eliminates the need for a separate finger sensor with its attendant cable. The sensor allows the insertion of any adult finger and that of children down to the age of about three. During use it is an integral part of the surrounding oximeter but can be readily removed and replaced by the user in the event of failure of the LEDs or photodetector. Its design enables it to be used with a variety of instruments from small saturation-only devices to larger multi-parameter instruments which can also measure temperature, end-tidal $CO_2$ or blood pressure.

A primary object of the invention is to provide a sensing module with the sensor having its own internal spring for gripping various size fingers, from those of large adults to children as young as three years of age.

A further object of the invention is to provide a sensing module which slides into a recess within an oximeter so that it is an integral part of the oximeter without the need for any external cords or cables.

Another object of the invention is to provide a sensing module which fits within the oximeter recess so securely that no special screws or latches are needed to hold it in place.

A further object of the invention is to provide a sensing module that can be used in many different types of monitoring devices. These can be small saturation-only instruments, devices measuring saturation and temperature, or devices measuring saturation, expired $CO_2$ or blood pressure.

Other objects and advantages of the invention will become apparent from the following description and drawings wherein:

DETAILED DESCRIPTION OF THE DRAWINGS

Figure 1:
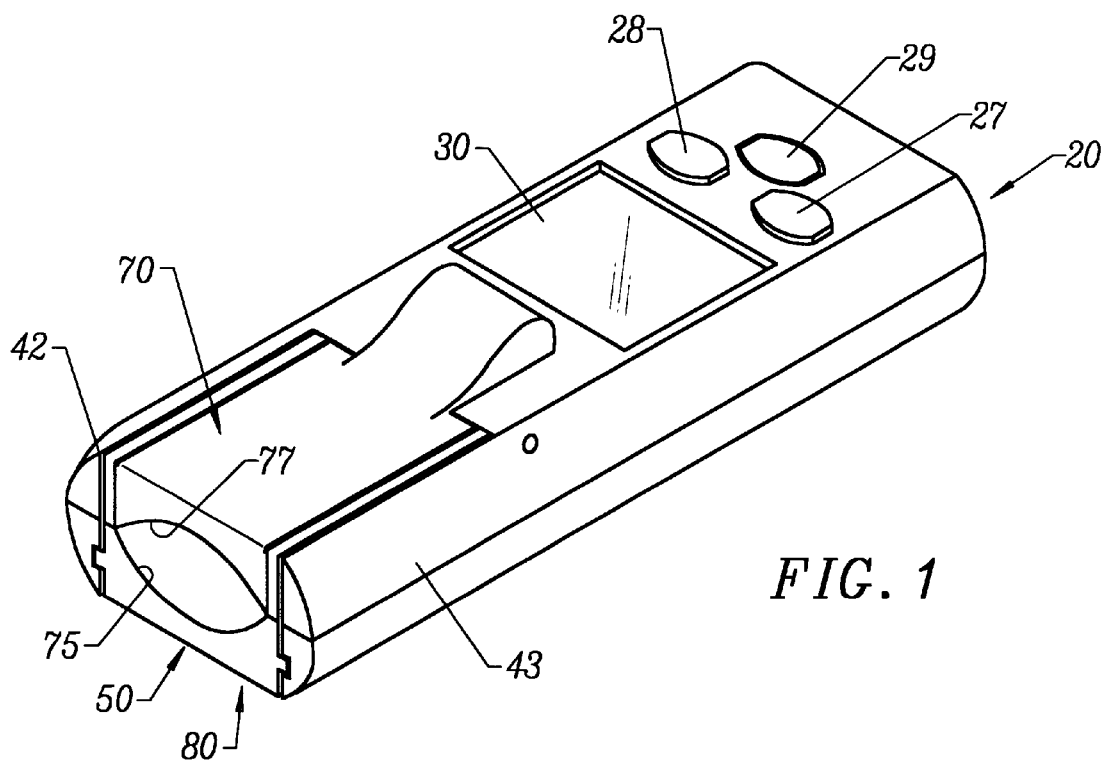
FIG. 1 shows the sensing module as used in a miniature pulse oximeter.
Figure 2:
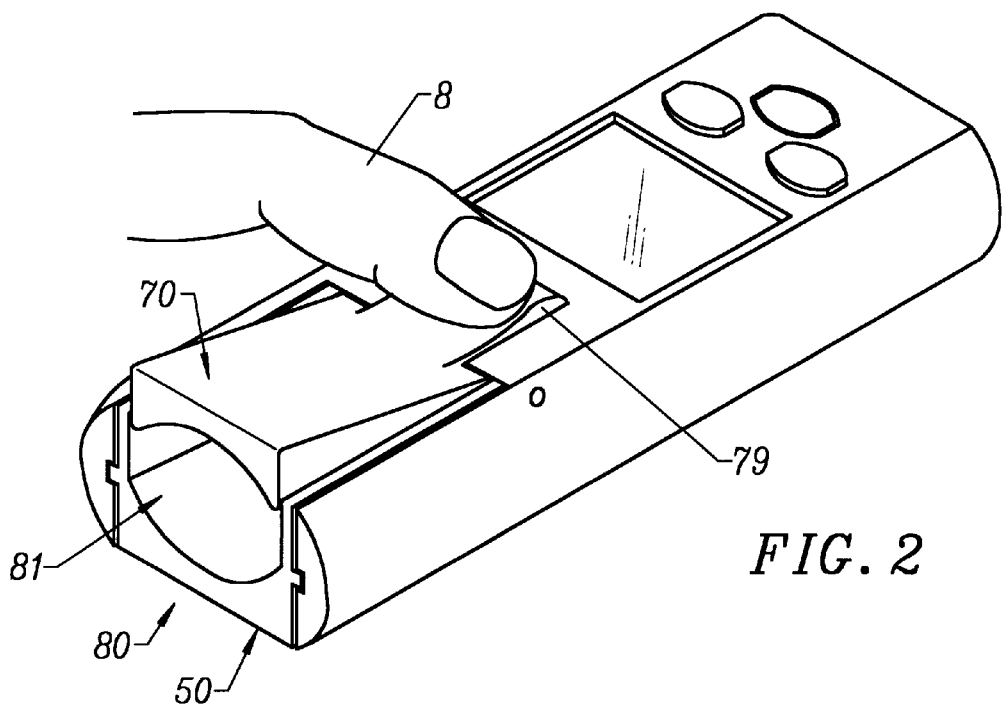
FIG. 2 shows the sensor being opened to allow insertion of a subject's finger.
Figure 3:
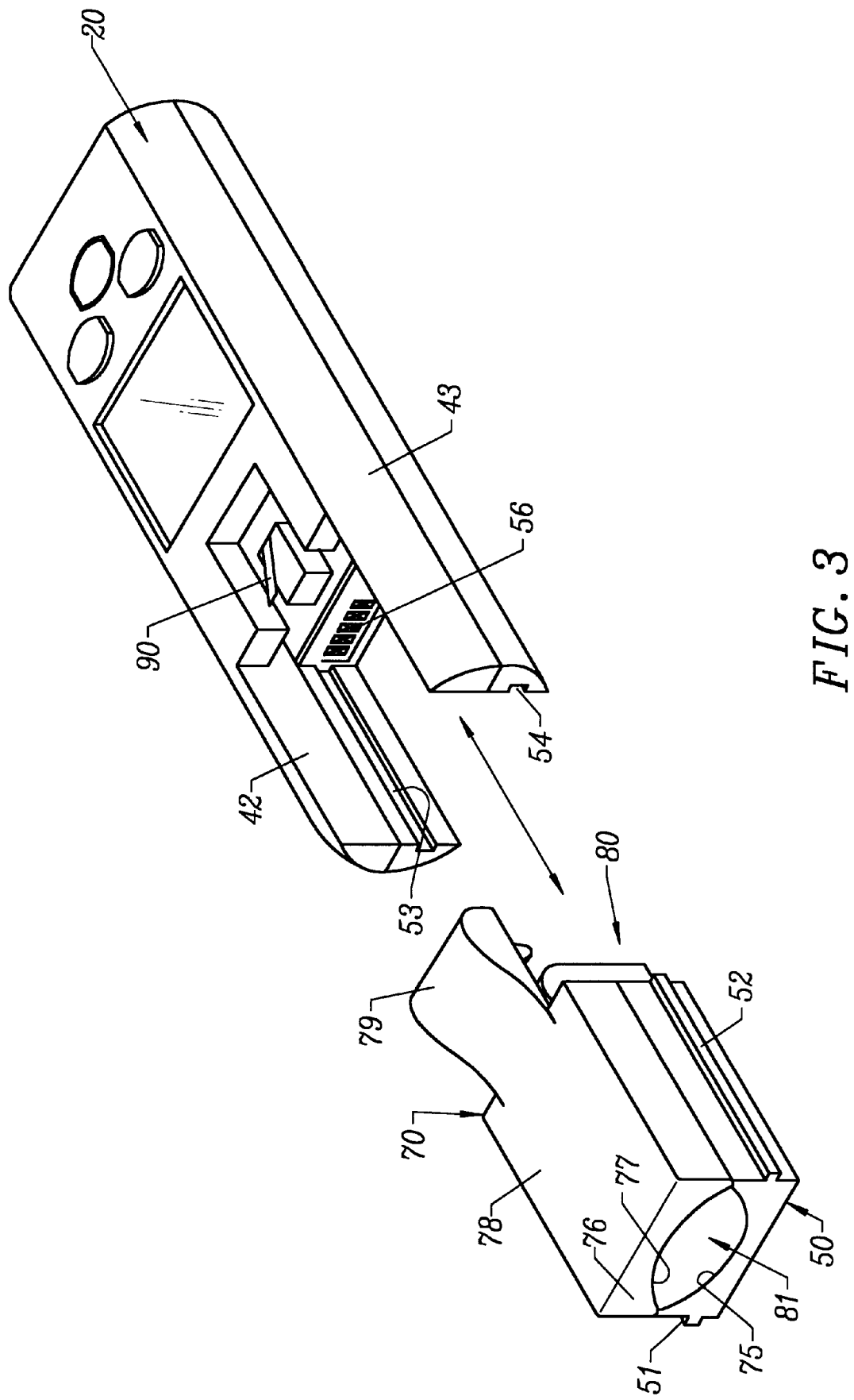
FIG. 3 shows the method by which the sensing module is removed from or inserted into the oximeter.

FIGS. 1–3 show a cordless miniature oximeter using the replaceable sensing module of the present invention. The body portion 20 carries an internal power supply, consisting of a single AAA battery, as well as pulse oximetry circuitry and memory. Circuitry and signal processing methods for pulse oximetry are now well known it the art.

Other aspects of the miniature pulse oximeter shown in FIGS. 1 & 2 are the LCD display 30, control buttons 27, 28 & 29 and the sensing module 80. FIG. 2 shows the movable top portion 70 of the module 80 being opened by the operators's finger 8 with pressure on knob 79 which stretches internal spring 92 (FIG. 7). When the operator's finger is lifted, tension of the internal spring causes a moderate gripping pressure on the patient's finger situated inside the sensor. LED's 85 (FIG. 9) are centrally mounted on the underside of the upper lid and a photodetector 86 (FIG. 9) is located in a directly opposite position facing upward on the lower fingertip pad 50. As shown in FIG. 3, the removable sensing module 80 is carried in a recess between arms 42 and 43 of body portion 20 by means of horizontal rails 51 & 52 that slide into reciprocal grooves 53 & 54, carried by arms 42 & 43, respectively. The rails may alternately be formed on arms 42 and 43 and reciprocal grooves formed on sensing module 80. Electrical connector pins 55 (FIG. 6) extend rearwardly from sensing module 80 and slidably engage electrical multi-pin socket 56 (FIG. 3) carried by oximeter body portion 20. Connector pins 55 and socket 56 allow the sensing module to be detachably connected to the electronic circuitry of the oximeter. The connector pins 55 and socket 56 also create a mechanical connection between the sensing module 80 and oximeter body 20, effectively preventing dislodgement of the attached sensing module. Sensing module 80 can be readily removed and replaced by a user without using any tools.

Fingertip pad 50 and fingertip cover 70 have concave surfaces 75 and 77, respectively with curvatures comfortable for the fingertip of an average adult user. Children as young as three can also utilize the sensor. A subject's finger is inserted into the receptacle 81 formed between this upper and lower halves of the sensor.

An upper half of the sensor shown generally as 70 is mounted above lower half 50 and is pivotally movable between an open position shown in FIG. 2 and a closed position shown in FIG. 3. As shown in FIG. 7, the upper enclosure 70 is pivotally joined to the lower enclosure 50 by means of an internal horizontal pin 71 which traverses two small holes 101 and 102 in the vertical supports 103 and 104, respectively, and one large obround hole 72 in the upper enclosure. The large obround hole 72 allows a desirable cam effect around the pin 71 which permits the pivoting upper lid 70 to elevate and accommodate a variety of finger sizes. Obround hole 72 is formed by a generally unshaped member 105 on the bottom of knob 79.

Fingertip enclosure 70 has a distal end 76 and a concave surface 77 forming its lower surface and a generally flat upper surface 78. The lower concave surface 75 cooperates with the upper surface of the fingertip pad to form a receptacle 81 (FIG. 2) for receiving the fingertip of a user. A knob 79 is carried by the proximal end of enclosure 70. The purpose of the knob is to allow a user to open the device to accept a patient's finger. Opening the sensor allows insertion of the subject's finger and also turns on the oximeter by closing the mechanical switch 90 from pressure on the switch by prominence 114 (FIG. 4).

Figure 4:
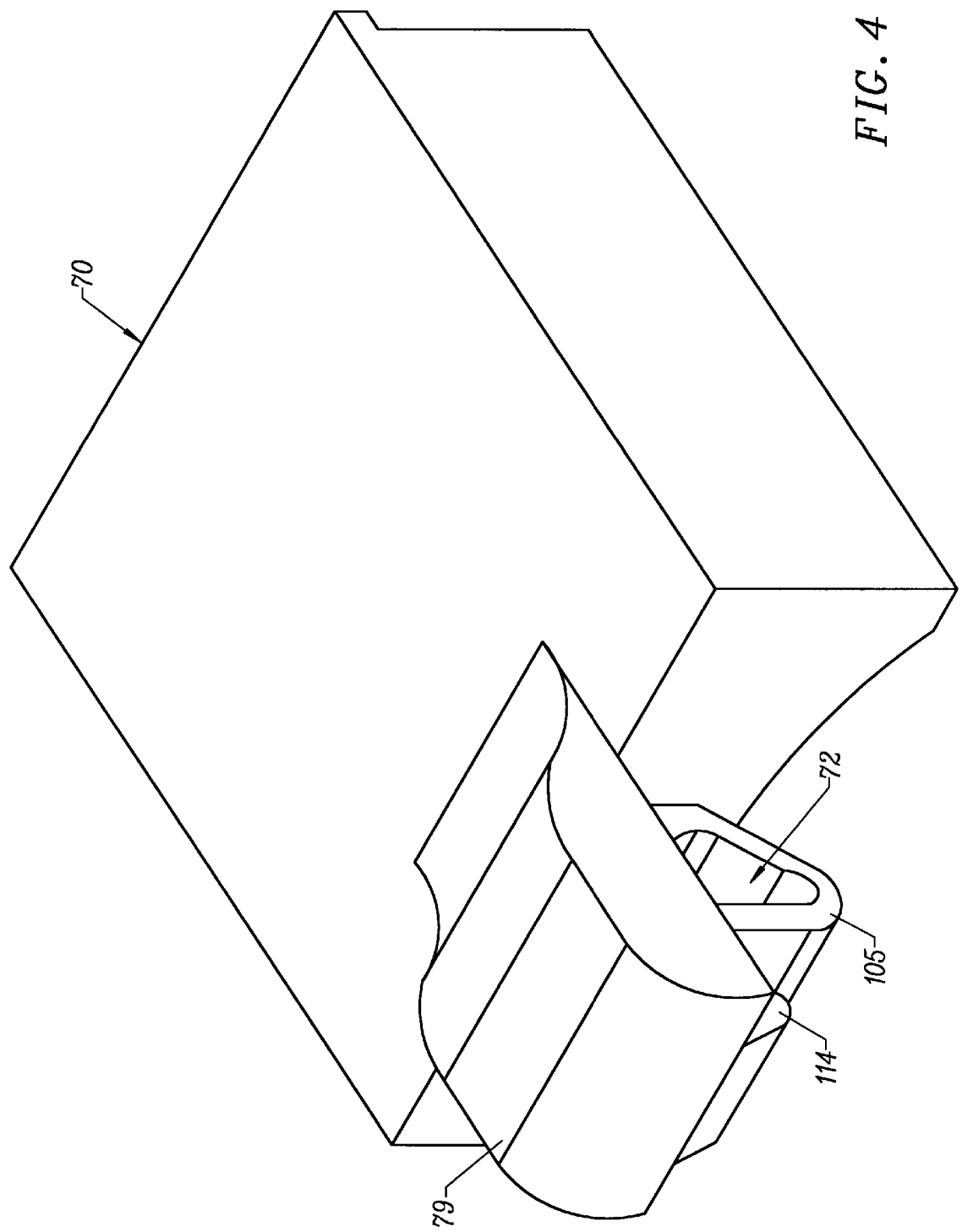
FIG. 4 is a top view of the upper fingertip enclosure which pivots and contains the LED assembly.

FIG. 4 is a top view of the upper fingertip enclosure 70 which lifts up upon insertion of a finger or with pressure of the operator onto knob 79. A prominence 114 on the under surface of the knob is located directly over a mechanical switch 90 which turns on the instrument as the lid is raised. The view of the underside of the upper enclosure 70 (FIG. 5) shows grooves 106 and 107 which hold the concave lid cover and circuit board for the LED assembly.

Figure 5:
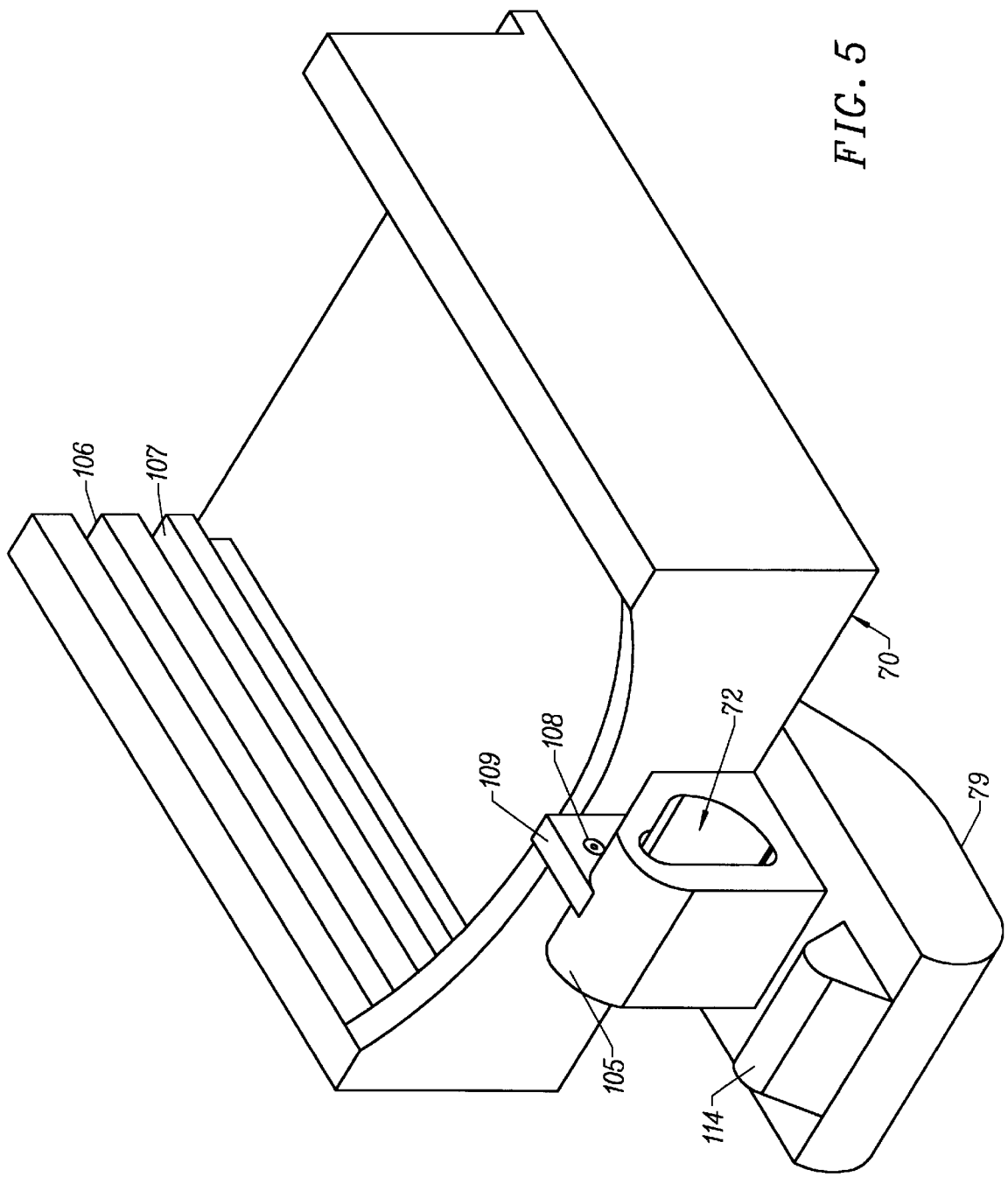
FIG. 5 is an internal view of the same fingertip cover of FIG. 4.
Figure 6:
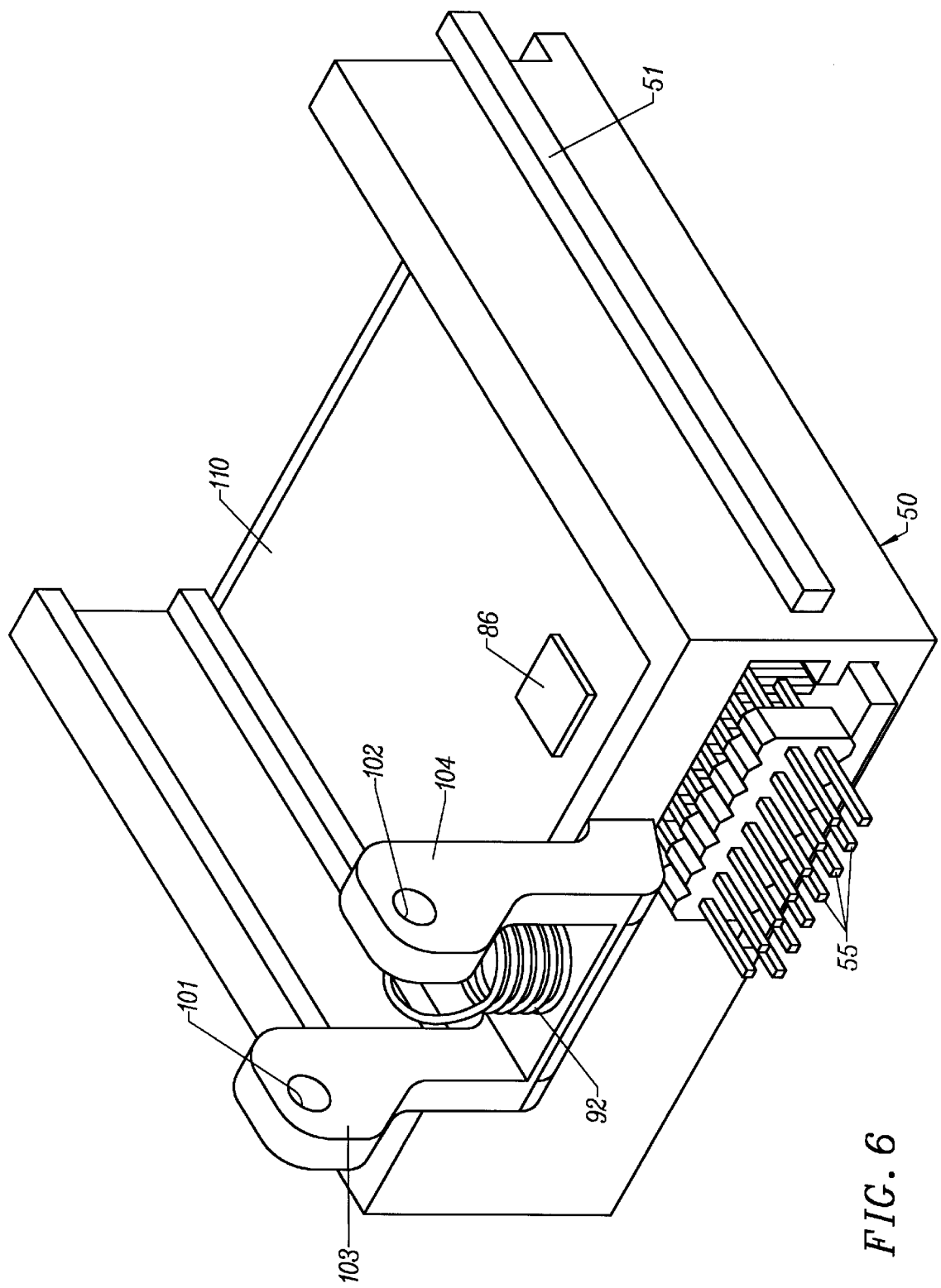
FIG. 6 is a view looking downward at the enclosure for the lower fingertip pad, showing the internal spring, the dual row pin connector and the side rails which stabilize this portion of the sensor when it is placed into the oximeter.
Figure 7:
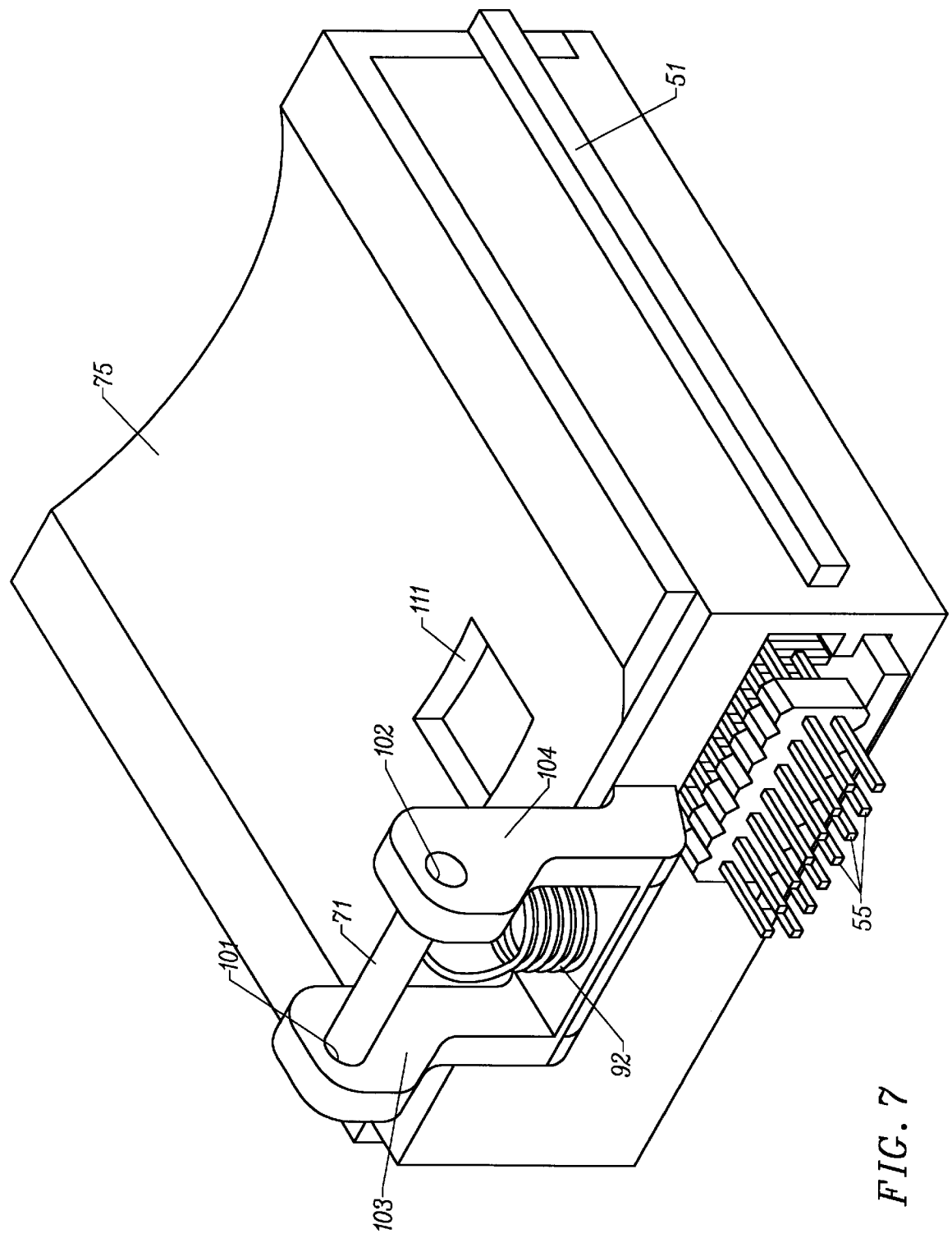
FIG. 7 shows the top surface of the lower enclosure and the placement of the photodetector.

FIG. 6 shows an internal view of the lower half 50 of the sensor module. A dual pin double row connector 55 plugs into a matching receptacle 56 when the module is inserted into the oximeter on rails 51 and 52. Internal spring 92 is located adjacent to and just forward of a pivot pin 71 which is held in the small holes 101 and 102. Internal spring 92 is oriented perpendicular to pin 71 so that spring 92 is stretched by an upward pivoting of upper enclosure 70. A small hole 108 in gusset 109 is for attachment of the upper end of the spring (FIG. 5). Shelf 110 holds a small circuit board containing the photodetector and an operational amplifier.

FIG. 7 shows concave fingerrest 75 closing the lower half 70 of the module. A rectangular opening 111 is for the transparent lens of the photodetector.

Figure 8:
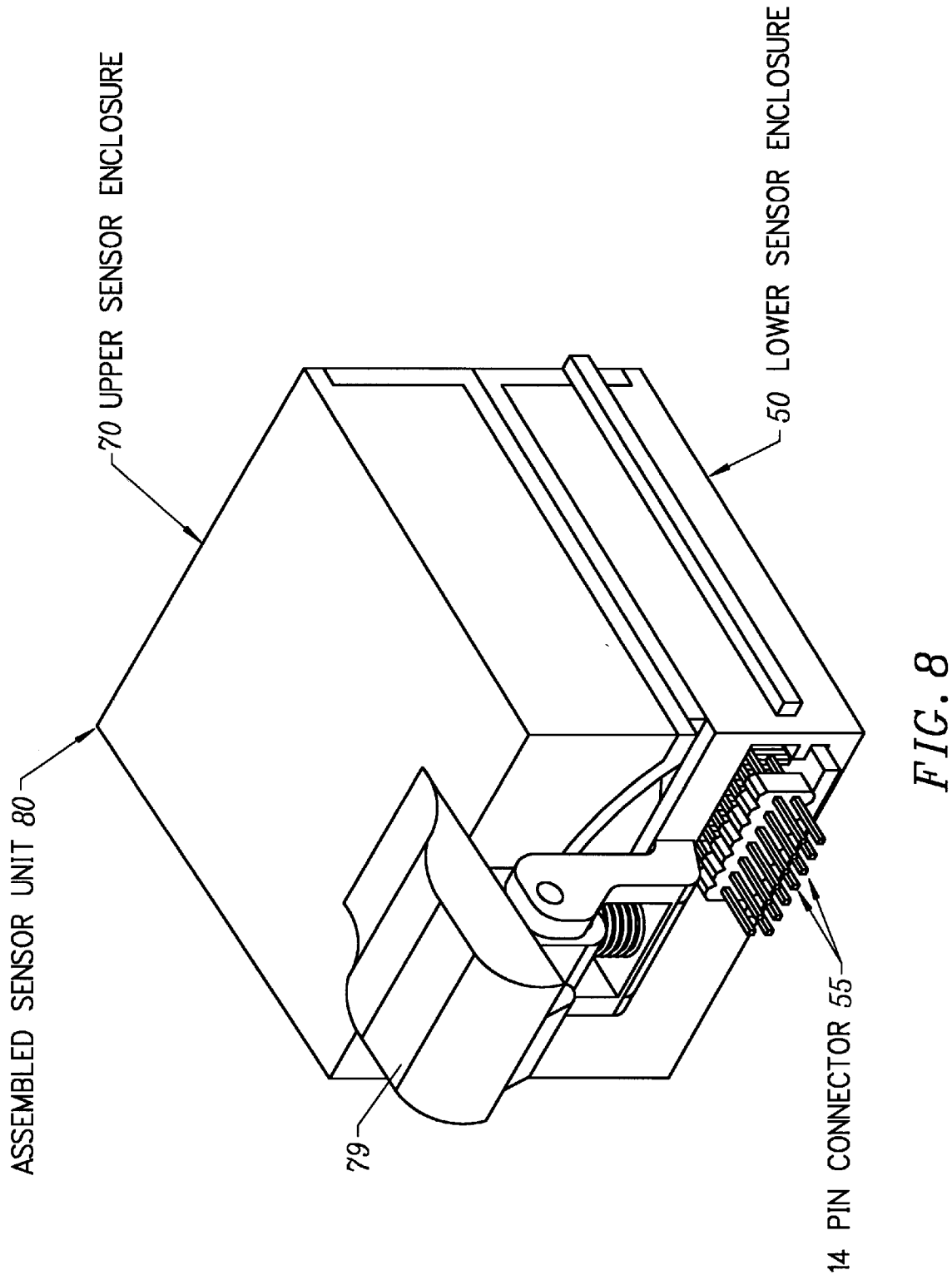
FIG. 8 is a view of the assembled sensor module.

FIG. 8 shows the assembled sensor module 80.

Figure 9:
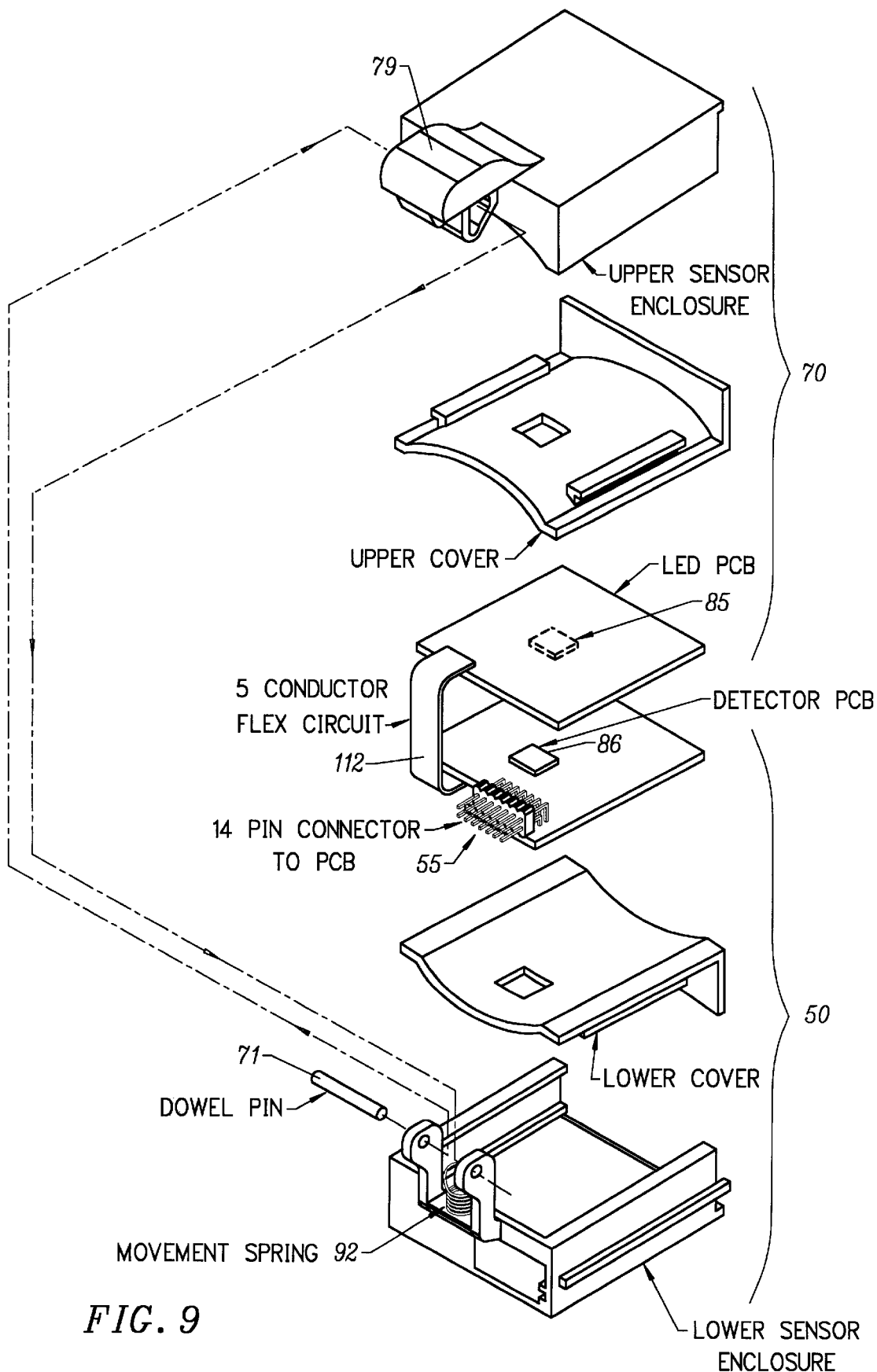
FIG. 9 is an expanded view of a disassembled sensor module showing the four major plastic parts and two circuit boards of which it is comprised.

FIG. 9 shows the disassembled sensor and its six major plastic parts. Flex circuit 112 provides the electrical connection between the two sensor module circuit boards and is shown in greater than actual length for clarity.

Figure 10:
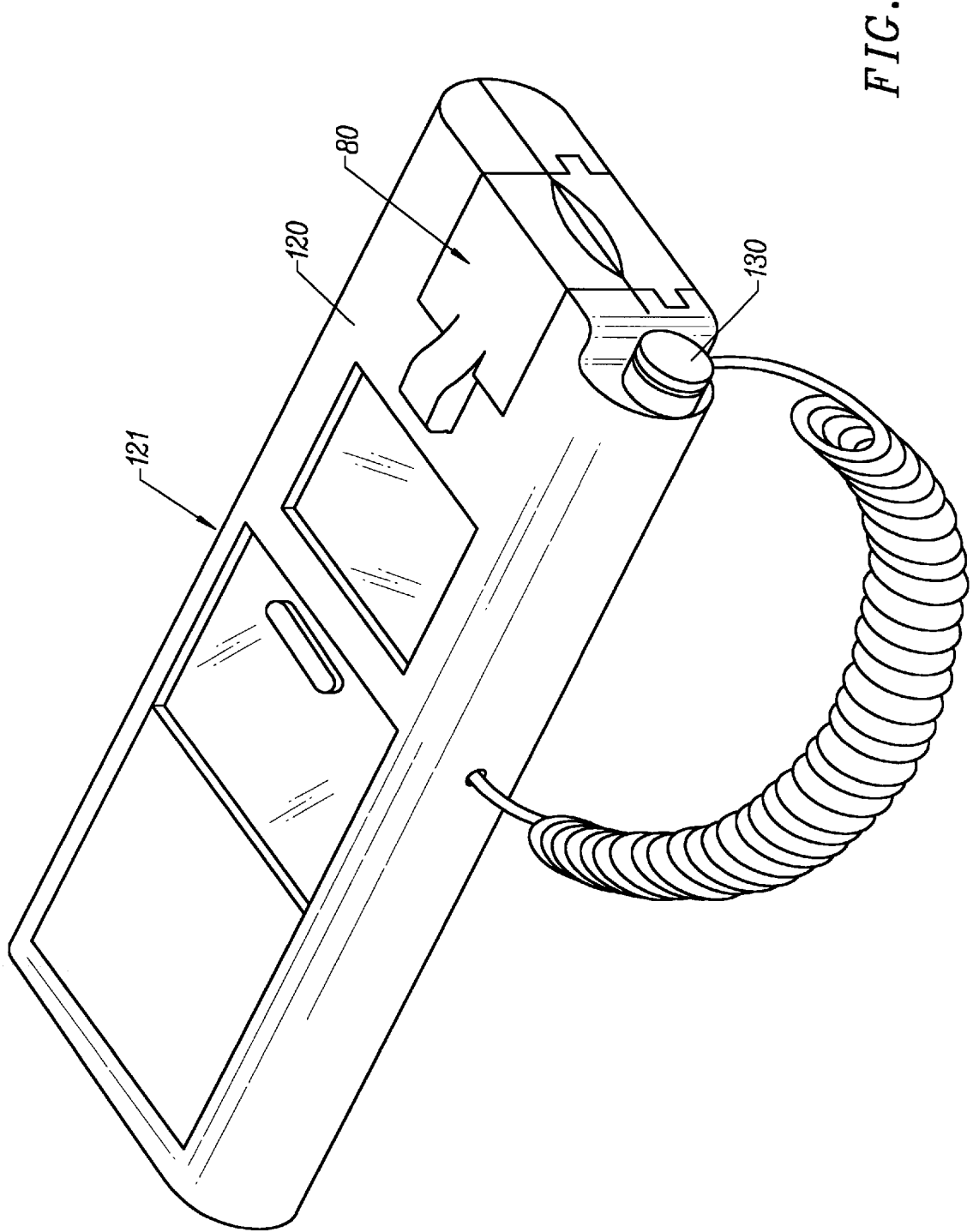
FIG. 10 shows a combination saturation and temperature monitor which uses the sensing module of the present invention.

FIG. 10 shows the sensing module 80 used in a combination pulse oximeter and thermometer 120. An elongated temperature probe 130 is carried by the housing 121, along with sterile probe covers. The same cordless sensing module can be readily adaptable to many other types of medical instruments such as combinations of O2 saturation with NIBP or end-tidal CO2 or cardiography.

Various design changes may be made without departing from the invention. For example, different internal spring mechanisms may be utilized, as well as different mounting mechanisms for detachably connecting the sensing module to the oximeter.

What is claimed is:

1. A cordless pulse oximeter, comprising:

a body portion carrying an internal power supply and pulse oximetry circuitry, a recess formed in said body portion, a sensing module removably carried in said recess, said sensing module including a lower enclosure and an upper enclosure mounted above said lower enclosure, said upper enclosure being pivotally movable between a closed position and an open position, said upper enclosure cooperating with said lower enclosure to form a receptacle adapted to receive the fingertip of a user, a first sensing element carried by said upper enclosure, and a second sensing element carried by said lower enclosure, means for removably attaching said sensing module into said recess in said body portion, and cordless means for detachably connecting said sensing module to said pulse oximeter circuitry in said body portion.

2. The apparatus of claim 1 wherein said means for removably attaching said sensing module to said body portion comprises a system of mounting rails and reciprocal grooves on said body portion and said sensing module to allow the sensing module to be readily attached or detached from said body portion.

3. The apparatus of claim 1 further comprising a mechanical on-off switch which is closed when said fingertip cover is in its open position and which is open when said fingertip cover is in its closed position.

4. The apparatus of claim 3 further comprising a prominence on the upper enclosure which rests on said mechanical switch.

* * * * *